United States Patent [19]

Pfliegel et al.

[11] 4,065,491
[45] Dec. 27, 1977

[54] PROCESS FOR THE PREPARATION OF N-PHOSPHONOMETHYL-GLYCINE

[75] Inventors: Tódor Pfliegel; Jenö Seres; Antal Gajáry; Klára Daróczy nee Csuka; Lajos T. Nagy, all of Budapest, Hungary

[73] Assignee: Chinoin Gyogyszer es Vegyeszeti Termekek Gyara Rt., Budapest, Hungary

[21] Appl. No.: 758,790

[22] Filed: Jan. 12, 1977

Related U.S. Application Data

[63] Continuation of Ser. No. 588,231, June 19, 1975, abandoned.

[30] Foreign Application Priority Data

June 27, 1974 Hungary .................................. 2251

[51] Int. Cl.$^2$ .............................................. C07F 9/38
[52] U.S. Cl. .............................. 260/502.5; 260/534 M
[58] Field of Search ......................... 260/502.5, 534 M

[56] References Cited

U.S. PATENT DOCUMENTS

| 2,635,112 | 4/1953 | Fields | 260/502.5 |
|---|---|---|---|
| 2,847,442 | 8/1958 | Sellman | 260/502.5 |
| 3,288,846 | 11/1966 | Irani et al. | 260/502.5 |
| 3,298,956 | 1/1967 | Irani et al. | 260/502.5 |
| 3,480,594 | 11/1969 | Price | 260/945 |

OTHER PUBLICATIONS

Walker, "Formaldehyde", 1944, p. 199.

*Primary Examiner*—Joseph E. Evans
*Attorney, Agent, or Firm*—Karl F. Ross

[57] ABSTRACT

The invention relates to a new and improved method for the preparation of N-phosphonomethyl-glycine, a potent pre-emergence herbicide. According to the invention glycine, formaldehyde and a dialkyl phosphite are condensed in an aqueous alkaline medium to form a N-phosphonomethyl-glycine dialkyl ester, and the diester is hydrolyzed with a mineral acid.

2 Claims, No Drawings

PROCESS FOR THE PREPARATION OF N-PHOSPHONOMETHYL-GLYCINE

This is a continuation of application Ser. No. 588,231, filed 19 June 1975 now abandoned.

This invention relates to a novel process for the preparation of N-phosphonomethyl-glycine.

The monosodium and mono-dimethylammonium salts of N-phosphonomethyl-glycine are known post-emergent herbicidal agents active against a wide variety of weeds. When used in an amount of 1 to 2 kg./ha., these compounds are very active against various perennial and annual monocotyledons (grass weeds), such as *Agropyron repens, Sorghum halepense, Cynodon dactylon, Cyperus spp., Festuca arundinacea, Taraxacum officiale,* and can be used for combatting these weeds e.g. in alfalfa, corn, fruit gardens, cultivated and industrial plants.

N-Phosphonomethyl-glycine is a non-toxic compound ($LD_{50}$ p.o. = 9800 mg./kg. on rats), quickly decomposing in the soil. Thus it can be applied to advantage even in crop rotation cultures (Baird, D.D. et al.: Proc. Annu. Calif. Weed Conf. 24, 94-102 1972, Chem. Abstr. 77, 97609 1972). When applied in closed-system corn cultures, the monoisopropylammonium salt of this compound has proven to be more effective than paraquate against Agropyron repens and Taraxacum officiale (Peters, R.A. et al.: Proc. N. E. Weed Sci. Soc. 27, 1-6 1973, Chem. Abstr. 78, 106886 1973).

According to the known processes, N-phosphonomethyl-glycine can be prepared by subjecting glycine to phosphonomethylation with e.g. chloromethylphosphonic acid or an ester thereof, by coupling phosphites onto azomethines, or by oxidizing N-phosphinomethyl-glycine (Belgian Pat. No. 774,349).

The synthesis utilizing azomethines must be carried out only in anhydrous media (Berichte 93, 2308 1960).

According to another known method, N-phosphonomethyl-glycine can be prepared by deacetylating di-N,N-carboxymethyl-aminomethyl-phosphonic acid with a strong acid (published Dutch Patent Application No. 73 03,948).

Now it has been found that N-phosphonomethyl-glycine can be prepared in a smooth and easily performable process by condensing glycine, formaldehyde and a dialkyl phosphite in an aqueous alkaline medium to form a N-phosphonomethyl-glycine dialkyl ester, and hydrolyzing this diester with a mineral acid. In the process according to the invention glycine, formaldehyde and the dialkyl phosphite are used preferably in equimolar amounts.

A further advantage of the process according to the invention is that the hydrolysis of the diester can be performed under far milder conditions than can hydrolysis of the tri-alkylesters. Namely, the respective tri-alkylesters can be hydrolyzed only with concentrated hydrobromic acid or another acid similar in strength, whereas according to the invention the hydrolysis proceeds even when using an aqueous mineral acid.

The N-phosphonomethyl-glycine dialkyl ester (preferably the respective methyl or ethyl ester) is prepared according to the invention in an aqueous alkali metal hydroxide preferably in an aqueous sodium hydroxide solution. The reaction of glycine and formaldehyde is conducted at a temperature between $-5°$ and $+15°$ C, preferably at 0° to 10° C. The obtained N-hydroxymethyl-glycine alkali metal salt (preferably sodium salt) is reacted without isolation with a dialkyl phosphite, preferably dimethyl or diethyl phosphite, at a temperature between 50° and 100° C, preferably at 90° to 100° C. This reaction yields the corresponding dialkyl ester of N-carboxymethyl-aminomethyl-phosphonic acid, which is then hydrolyzed with a mineral acid, preferably with concentrated hydrochloric acid, phosphoric acid or sulfuric acid. The hydrolysis is performed preferably at 50° to 100° C, particularly at 90° to 100° C.

It is not necessary to isolate the dialkyl ester prior to hydrolysis. The desired product can be obtained with good yield and high degree of purity when acidifying and boiling the reaction mixture.

The dialkyl phosphite starting substances can be prepared by reacting phosphorous trichloride with an appropriate alcohol (H. McCombie, B. C. Saunders, G. J. Stacey: J. Chem. Soc. 1945, 380).

The invention is elucidated in detail by the aid of the following Examples.

EXAMPLE 1

8.6 g. of 37% formaline (= 0.1 moles of formaldehyde) are added to a stirred solution of 4.0 g. (0.1 moles) of sodium hydroxide and 7.5 g. (0.1 moles) of glycine in 40 ml. of water at 0° to 5° C. After 10 minutes of stirring 11 g. (0.1 moles) of dimethyl phosphite are added, and stirring is continued for 2 hours at 90° to 100° C. The reaction mixture is cooled, acidified with hydrochloric acid, and extracted to obtain dimethyl N-carboxymethyl-aminomethyl-phosphonate. The hygroscopic product melts at 73°-75° with decomposition.

Analysis: Calculated: C: 30.4%; H: 6.9%; N: 7.1%; P: 15.7%; Found: C: 29.80%; H: 6.23%; N: 6.95%.

EXAMPLE 2

8.6 g. of 37% formaline (= 0.1 moles of formaldehyde) are added to a stirred solution of 4.0 g. (0.1 moles) of sodium hydroxide and 7.5 g. (0.1 moles) of glycine in 40 ml. of water. After 10 minutes of stirring at 0° to 5° C, 13.8 g. (0.1 moles) of diethyl phosphite are added, and stirring is continued for 2 hours at 90° to 100° C. The reaction mixture is cooled, acidified with hydrochloric acid, and extracted to obtain diethyl N-carboxymethyl-aminomethyl-phosphonate. The product melts at 132°-134° C with decomposition.

Analysis: Calculated: C: 37.3%; H: 7.1%; N: 6.2%; P: 13.8%; Found: C: 37.20%; H: 6.91%; N: 6.81%.

EXAMPLE 3

60 ml. of concentrated hydrochloric acid are added to 9.85 g. (0.05 moles) of N-carboxymethyl-aminomethyl-phosphonic acid dimethyl ester, and the mixture is boiled for 2 hours. The reaction mixture is concentrated to one-fourth volume under a pressure of 80 to 100 mmHg., and the oily residue is triturated with 60 ml. of methanol. The solid substance is filtered when cold, dissolved in 15 to 20 ml. of hot water; the solution is decolorized, cooled, and the product is precipitated with 45 ml. of acetone. 5.5-5.65 g. (65-67%) of N-phosphonomethyl-glycine are obtained; m.p.: 224°-225° C (with decomposition).

Analysis: Calculated: C: 21.30%; H: 4.72%; N: 8.28%; Found: C: 21.22%; H: 4.66%; N: 8.08%.

EXAMPLE 4

60 ml. of concentrated hydrochloric acid are added to 11.25 g. (0.05 moles) of diethyl N-carboxymethyl-aminomethyl-phosphonate, and the mixture is boiled for 2 hours. The reaction mixture is concentrated to one-fourth volume under a pressure of 80 to 100 mmHg., and the residue is triturated with 60 ml. of ethanol. The solid substance is filtered when cold, dissolved in 15 to 20 ml. of hot water, the solution is decolorized, cooled, and the product is precipitated with 45 ml. of acetone. 5.3–5.7 g. (62.7–67.5%) of N-phosphonomethyl-glycine are obtained.

Analysis: Calculated: C: 21.30%; H: 4.72%; N: 8.28%; Found: C: 21.29%; H: 4.73%; N: 8.12%.

EXAMPLE 5

8.6 g. of 37% formaline (= 0.1 moles of formaldehyde) are added to a stirred solution of 4.0 g. (0.1 moles) of sodium hydroxide and 7.5 g. (0.1 moles) of glycine in 40 ml. of water. After 10 minutes of stirring at 0° to 5° C, 11 g. (0.1 moles) of dimethyl phosphite are added, and stirring is continued for 2 hours at 90° to 100° C. The mixture is acidified with 60 ml. of concentrated hydrochloric acid, and stirred for further 2 hours at 90° to 100° C. The obtained solution is evaporated to dryness under reduced pressure (80 to 100 mmHg.). The oily residue is boiled with 200 ml. of 90% ethanol, the mixture is cooled, the product is filtered off, and dissolved in 30 to 35 ml. of hot water. The solution is decolorized, filtered, and the product is precipitated from the filtrate with 45 ml. of acetone. 11.0–11.3 g. (65–67%) of N-phosphonomethyl-glycine are obtained: m.p.: 224°–225° C (with decomposition).

Analysis: Calculated: C: 21.30%; H: 4.72%; N: 8.28%; Found: C: 21.17%; H: 4.63%; N: 8.15%.

EXAMPLE 6

8.6 g. of 37% formaline (= 0.1 moles of formaldehyde) are added to a stirred solution of 4.0 g. (0.1 moles) of sodium hydroxide and 7.5 g. (0.1 moles) of glycine in 40 ml. of water. After 10 minutes of stirring at 0° to 5° C, 13.8 g. (0.1 moles) of diethyl phosphite are added, and stirring is continued for 2 hours at 90° to 100° C. The mixture is acidified with 60 ml. of concentrated hydrochloric acid, and stirred further for 2 hours at 90° to 100° C. The obtained solution is evaporated to dryness under reduced pressure (80 to 100 mmHg.). The oily residue is treated with 200 ml. of warm 90% ethanol, the mixture is cooled, the product is filtered off, and dissolved in 30 to 35 ml. of hot water. The solution is decolorized, filtered, and the product is precipitated from the filtrate with 45 ml. of acetone. 11.0–11.4 g. (65–67.5%) of N-phosphonomethyl-glycine are obtained; m.p.: 224°–226° C (with decomposition).

Analysis: Calculated: C: 21.30%; H: 4.72%; N: 8.28%; Found: C: 21.15%; H: 4.60%; N: 8.11%.

What we claim is:

1. A process for the preparation of N-phosphonomethyl-glycine comprising the steps of:
    a. reacting formaldehyde and glycine in an aqueous alkali-metal hydroxide medium in substantially equimolar quantities at a temperature of $-5°$ to $+15°$ C;
    b. adding to the reaction system of step (a) an amount of dimethyl or diethyl phosphite substantially equimolar to the glycine and formaldehyde;
    c. heating the reaction system of step (b) to a temperature of 50° to 100° C to form N-phosphonomethyl-glycine dimethyl or diethylester; and
    d. hydrolyzing the diester formed in step (c) by adding to the reaction system thereof at a temperature between 50° and 100° C a mineral acid selected from the group which consists of hydrochloric acid, sulfuric acid and phosphoric acid, thereby producing N-phosphonomethyl-glycine.

2. The process defined in claim 1 wherein the alkali-metal hydroxide is sodium hydroxide.

* * * * *